US012797478B2

(12) United States Patent
Hara et al.

(10) Patent No.: US 12,797,478 B2
(45) Date of Patent: Nov. 17, 2026

(54) POLYMER HAVING HALOGEN-CONTAINING SEGMENT AND PHARMACEUTICAL COMPOSITION USING SAME

(71) Applicants: AGC INC., Tokyo (JP); THE UNIVERSITY OF TOKYO, Tokyo (JP); NATIONAL UNIVERSITY CORPORATION TOKYO MEDICAL AND DENTAL UNIVERSITY, Tokyo (JP)

(72) Inventors: Mihoko Hara, Tokyo (JP); Rintaro Hara, Tokyo (JP); Kanjiro Miyata, Tokyo (JP); Mitsuru Naito, Tokyo (JP); Takanori Yokota, Tokyo (JP)

(73) Assignees: AGC INC., Tokyo (JP); THE UNIVERSITY OF TOKYO, Tokyo (JP); NATIONAL UNIVERSITY CORPORATION TOKYO MEDICAL AND DENTAL UNIVERSITY, Tokyo (JP)

(*) Notice: Subject to any disclaimer, the term of this patent is extended or adjusted under 35 U.S.C. 154(b) by 574 days.

(21) Appl. No.: 18/463,711

(22) Filed: Sep. 8, 2023

(65) Prior Publication Data

US 2023/0414765 A1 Dec. 28, 2023

Related U.S. Application Data

(63) Continuation of application No. PCT/JP2022/009642, filed on Mar. 7, 2022.

(30) Foreign Application Priority Data

Mar. 10, 2021 (JP) ................................ 2021-038762

(51) Int. Cl.
*A61K 47/59* (2017.01)
*A61K 47/60* (2017.01)
*C08G 69/48* (2006.01)

(52) U.S. Cl.
CPC ............ *A61K 47/595* (2017.08); *A61K 47/60* (2017.08); *C08G 69/48* (2013.01)

(58) Field of Classification Search
CPC ......... C08G 69/08; C08G 69/10; C08G 69/42
See application file for complete search history.

(56) References Cited

U.S. PATENT DOCUMENTS

| | | | | |
|---|---|---|---|---|
| 6,677,164 B1 * | 1/2004 | Thoma | ................. | C07K 14/001 530/391.1 |
| 2009/0232762 A1 * | 9/2009 | Xiong | ................ | A61K 31/7088 514/772.3 |
| 2014/0017328 A1 | 1/2014 | Kataoka et al. | | |
| 2015/0051347 A1 * | 2/2015 | Kataoka | ................. | A61K 47/60 525/435 |
| 2018/0289835 A1 | 10/2018 | Kataoka et al. | | |
| 2018/0334674 A1 | 11/2018 | Kondo et al. | | |

FOREIGN PATENT DOCUMENTS

| | | | |
|---|---|---|---|
| JP | 3-2217 | A | 1/1991 |
| JP | 11-509861 | A | 8/1999 |
| JP | 2011-231220 | A | 11/2011 |
| JP | 2019-45729 | A | 3/2019 |
| WO | WO 2012/096399 | A1 | 7/2012 |
| WO | WO 2016/186204 | A1 | 11/2016 |
| WO | WO 2017/086467 | A1 | 5/2017 |
| WO | WO 2020/218481 | A1 | 10/2020 |

OTHER PUBLICATIONS

Guillermain, Macromol. Chem. Phys. 2002, 203, 1346-1356 (Year: 2002).*
Chen, J. Appl. Polym. Sci. 2021:138, p. 1-13. (Year: 2021).*
International Search Report issued May 31, 2022, in PCT/JP2022/009642 (with English Translation), 2 pages.
Long-Hai Wang et al., "High DNA-Binding Affinity and Gene-Transfection Efficacy of Bioreducible Cationic Nanomicelles with a Fluorinated Core", Angew. Chem. Int. Ed. 2016, 55, pp. 755-759.
Ting Wu et al., "Fluorinated PEG-Polypeptide Polyplex Micelles Have Good Serum-Resistance and Low Cytotoxicity for Gene Delivery", Macromol. Biosci. 2017, 17, 1700114, 8 pages.
Echuan Tan et al., "Statistical versus block fluoropolymers in gene Delivery", J. Mater. Chem. B, 2018, 6, pp. 7230-7238.
Gang Chen et al., "Reversibly Stabilized Polycation Nanoparticles for Combination Treatment of Early- and Late-Stage Metastatic Breast Cancer", ACS Nano 2018, 12, pp. 6620-6636.
Extended European Search Report issued Feb. 17, 2025 in European Patent Application No. 22767063.5, 16 pages.
Wang et al., "In Vivo Tracking of Fluorinated Polypeptide Gene Carriers by Positron Emission Tomography Imaging", ACS Applied Materials & Interfaces, vol. 12, 2020 pp. 54763-54771.
Lv et al., "Fluorination on Polyethyleneimine allows efficient 2D and 3D cell culture gene delivery", Journal of Materials Chemistry B, vol. 3, 2015, pp. 642-650.

(Continued)

*Primary Examiner* — Robert C Boyle
(74) *Attorney, Agent, or Firm* — Oblon, McClelland, Maier & Neustadt, L.L.P.

(57) ABSTRACT

A polymer represented by the following formula (I):

(I)

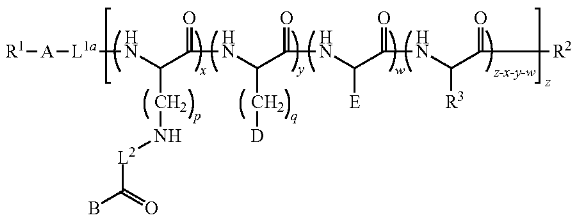

wherein each symbol is as described in the specification, is useful as a drug carrier in effectively delivering a drug to a target site.

7 Claims, 2 Drawing Sheets

(56) References Cited

OTHER PUBLICATIONS

Japanese Notice of Reasons for Refusal issued Jul. 2, 2024 in Japanese Application No. 2023-505529 with English Machine translation, 6 pgs.

* cited by examiner

[Fig. 1]
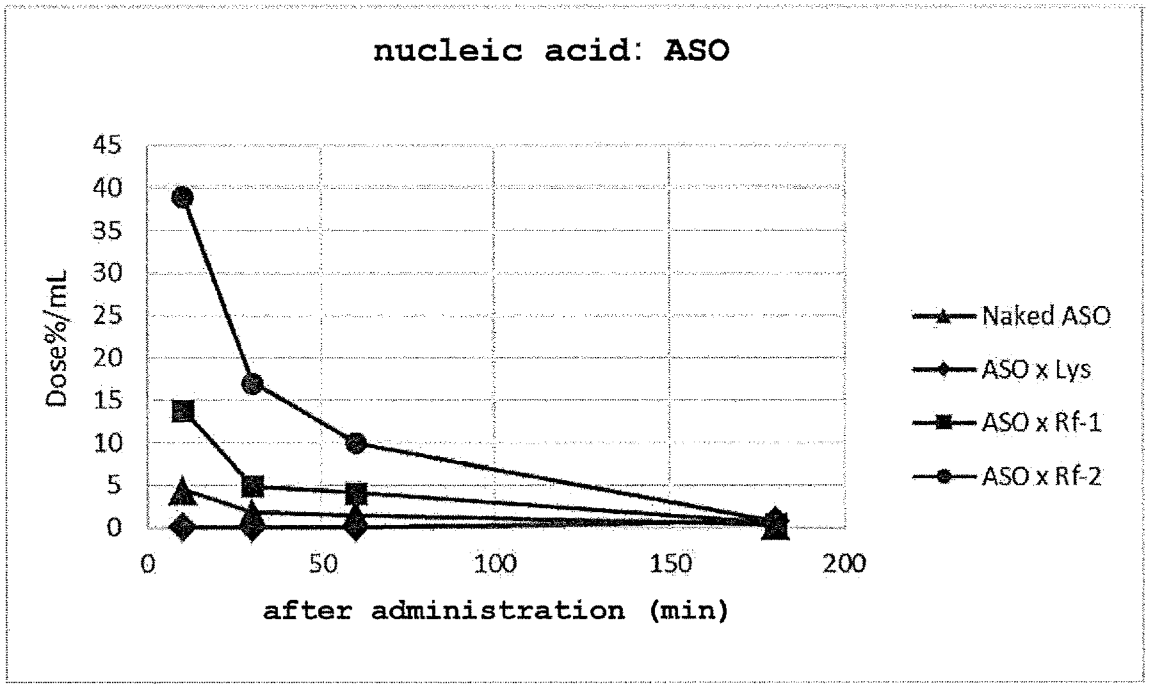
[Fig. 2]
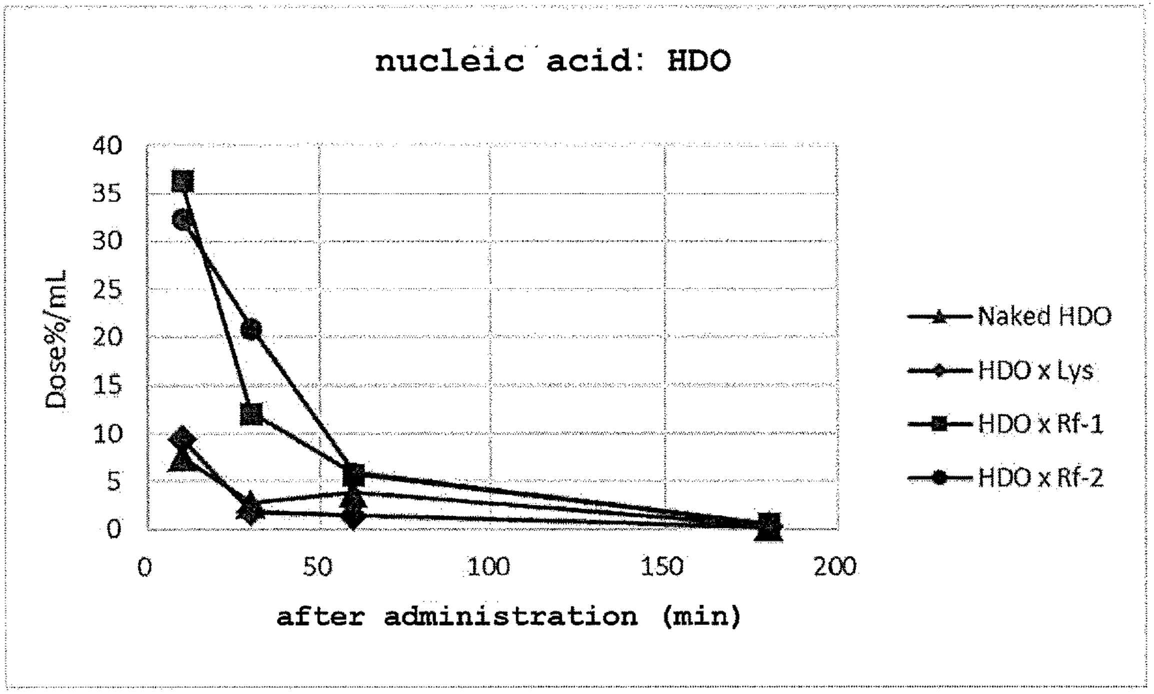

[Fig. 3]
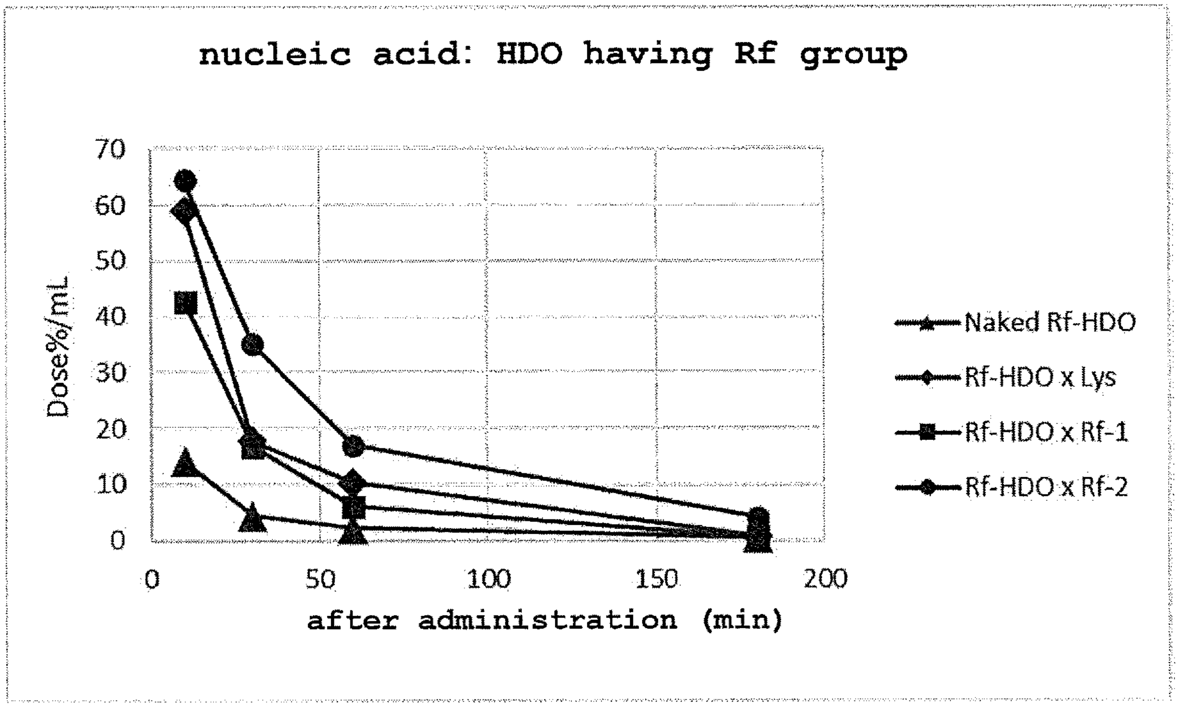

POLYMER HAVING HALOGEN-CONTAINING SEGMENT AND PHARMACEUTICAL COMPOSITION USING SAME

CROSS REFERENCES TO RELATED APPLICATIONS

This application is a continuation of International Patent Application No. PCT/JP2022/009642, filed on Mar. 7, 2022, and claims priority to Japanese Patent Application No. 2021-038762, filed on Mar. 10, 2021, both of which are incorporated herein by reference in their entireties.

BACKGROUND OF THE INVENTION

Field of the Invention

The present invention relates to a polymer useful as a carrier in delivering a drug effectively to a target site.

Discussion of the Background

Drugs that are required to exhibit efficacy effectively at target sites, such as nucleic acid medicines, can regulate various genes in cells. It is therefore strongly expected to be applied to various diseases such as cancer and hereditary diseases, which have been considered difficult to treat. On the other hand, nucleic acid drugs require an appropriate technology for delivery to the target cells (DDS technology) because the nucleic acid molecule itself has low stability in vivo.

As a nucleic acid delivery technology, for example, techniques have been disclosed in which a block copolymer having a hydrophilic polymer segment and a cationic polymer segment is used and a complex (polyion complex) is formed via electrostatic interactions between a nucleic acid and the block copolymer (see WO 2012/096399, WO 2017/086467, each of which is incorporated herein by reference in its entirety). Even though the WO 2012/096399 and WO 2017/086467 describe superior nucleic acid drug delivery technologies, a block copolymer containing a polymer segment with a specific structure having an alkyl group substituted with one or more halogen atoms (also denoted as a "haloalkyl group") in a side chain is not described.

Regarding DDS technology, Angew. Chem. Int. Ed. 2016, 55, 755-759, Macromol. Biosci. 2017, 17, 1700114, and Mater. Chem. B, 2018, 6, 7230-7238, each of which is incorporated herein by reference in its entirety, describe block copolymers having haloalkyl groups. However, the polymer of the present invention having specific structures represented by formulas (I) to (IV) mentioned below are not described or suggested.

SUMMARY OF THE INVENTION

DDS technology for drugs that is required to exhibit drug efficacy effectively in the target organ (target site) is required to have three functions: 1) a function to intensively deliver a drug to the lesion site, 2) a function to appropriately control the release of a drug from a preparation, and 3) a function to improve the targeted-cellular uptake efficiency of a drug by improving absorbability of a drug through the sikin and the mucous membranes such as the intestinal tract, and permeability through the blood-brain barrier. However, improvements in these functions have not always been satisfactory in the conventional DDS technology. The present invention aims to solve such problems in the DDS

TECHNICAL FIELD

As a result of intensive studies, the present inventors envisaged a polymer segment with a specific structure having a haloalkyl group in the side chain and found that the above-mentioned problems can be solved by the polymer alone or the polymer in combination with a hydrophilic polymer segment and/or a polycationic segment. Furthermore, they also found that a drug having a haloalkyl group can form a more stable complex with the polymer and completed the present invention.

Specifically, the present invention provides the following.

[1] A polymer represented by the following formula (I), (II), (III), or (IV)

(I)

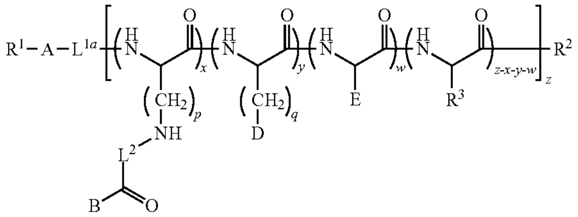

(II)

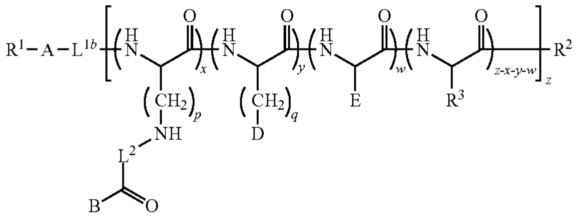

(III)

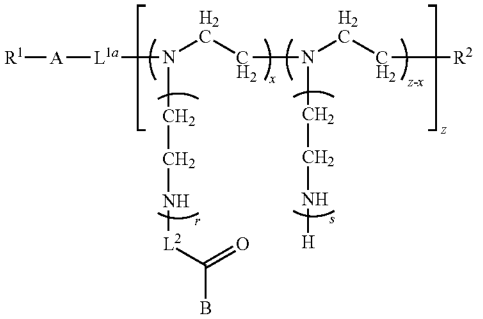

(IV)

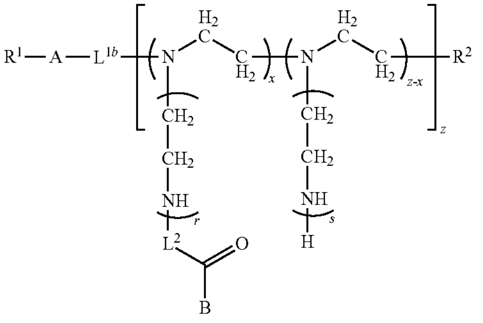

wherein $R^1$ and $R^2$ are each independently a hydrogen atom or an optionally substituted $C_{1-12}$ alkyl group, $R^3$ is a side chain of any amino acid, A is a single bond or a hydrophilic polymer chain, $L^{1a}$ and $L^{1b}$ are each independently a single bond or a linking group, $L^2$ is a single bond or $L^3$, $L^3$ is a linker represented by the formula (V) or (VI):

(V)

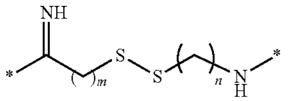

(VI)

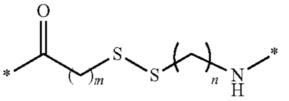

wherein m and n are each independently an integer of 0 to 5,

* on the left side is a bonding position to an —NH— group, and

* on the right side is a bonding position to a carbonyl group,

B is a $C_{1-20}$ haloalkyl group,

D is a cation-containing group, an anion-containing group, or a group represented by the formula (VII):

(VII)

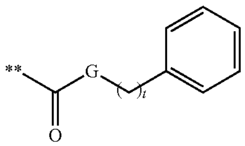

wherein t is an integer of 0 to 5,

** is a bonding position to a $—(CH_2)_q—$ group, and

G is O or NH,

E is an NHCOR group, an NHCOOR group, a CONHR group, or a COOR group,

R is an alkyl group having 3 to 20 carbon atoms or a group derived from a lipid, z is an integer of 2 to 500, x is an integer that is not less than 40% of z, y is an integer that may be 0, w is an integer that may be 0, z-x-y-w is an integer that may be 0, z-x is an integer that may be 0, p, q and r are each independently an integer of 1 to 10, and s is an integer of 0 to 10.

(provided that, in the formulas (III) and (IV), (i) when A is a single bond, (ii) m is an integer of 0 to 2).

[2] The polymer of the above-mentioned [1], wherein, in the formula (I) or (II), a total of x, y, and w is not less than 95% of z.

[3] The polymer of the above-mentioned [1] or [2], wherein A is a hydrophilic polymer chain.

[4] The polymer of the above-mentioned [1] or [2], wherein A is a single bond.

[5] The polymer of any of the above-mentioned [1] to [4], wherein B is a $C_{1-20}$ fluoroalkyl group.

[6] The polymer of the above-mentioned [5], wherein B is a $C_{1-20}$ alkyl group in which all hydrogen atoms are substituted with fluorine atoms.

[7] A polymer-drug complex comprising a polymer of any of the above-mentioned [1] to [6] and a drug, wherein the polymer and the drug form a complex.

[8] The polymer-drug complex of the above-mentioned [7], wherein the drug is a biopolymer.

[9] A medicament comprising the polymer-drug complex of the above-mentioned [7] or [8] as an active ingredient.

Advantageous Effects of Invention

The present invention provides a polymer useful as a carrier in delivering a drug effectively to a target site.

BRIEF DESCRIPTION OF THE DRAWINGS

FIG. 1 shows the evaluation results when ASO was used as a nucleic acid in the animal experiments relating to retention property in blood to be described later.

FIG. 2 shows the evaluation results when HDO was used as a nucleic acid in the animal experiments relating to retention property in blood to be described later.

FIG. 3 shows the evaluation results when HDO modified by a haloalkyl group was used as a nucleic acid in the animal experiments relating to retention property in blood to be described later.

DETAILED DESCRIPTION OF THE PREFERRED EMBODIMENTS

The present invention is described in detail below according to embodiments.

Unless otherwise specified in the sentences, any technical terms and scientific terms used in the present specification, have the same meaning as those generally understood by those of ordinary skill in the art the present invention belongs to. Any methods and materials similar or equivalent to those described in the present specification can be used for practicing or testing the present invention, and preferred methods and materials are described in the following. All publications and patents referred to in the present specification are hereby incorporated by reference so as to describe and disclose constructed products and methodology described in, for example, publications usable in relation to the described invention.

The polymer used in the present invention may exhibit some degree of polydispersity when obtained as a polymerization reaction product. In the present specification, therefore, when reference is made to polymer properties (molecular weight, degree of polymerization, electric charge, etc.), they refer to the average of the whole polymerization reaction product showing polydispersity, unless otherwise specified.

In the polymers represented by the formulas (I) to (IV) in the present specification, structurally corresponding groups and moieties are defined using the same symbols, for example, $R_1$, A, B, x, y, z, and the like. These groups and moieties are independent of each other among the respective polymers (I) to (IV). Therefore, for example, preferred embodiments of groups or moieties represented by the same symbol may be the same or different for each polymer (e.g., between polymers (I) and (II)).

I. Polymers Represented by the Formulas (I) to (IV) of the Present Invention

The present invention provides polymers represented by the following formulas (I), (II), (III), and (IV) (sometimes collectively referred to as "the polymer of the present invention" in the present specification).

(I)

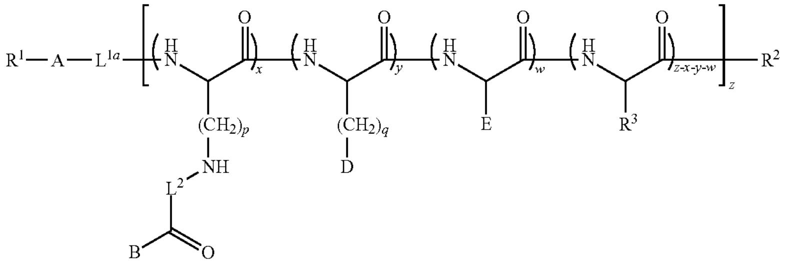

(II)

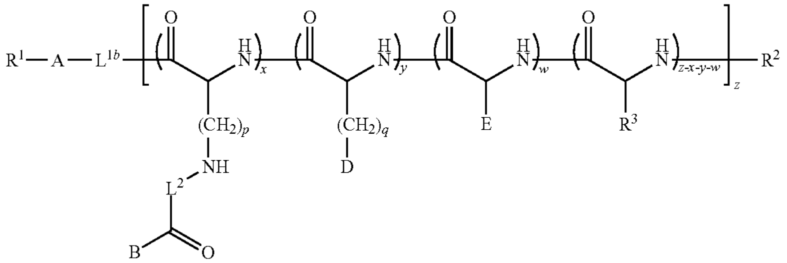

(III)

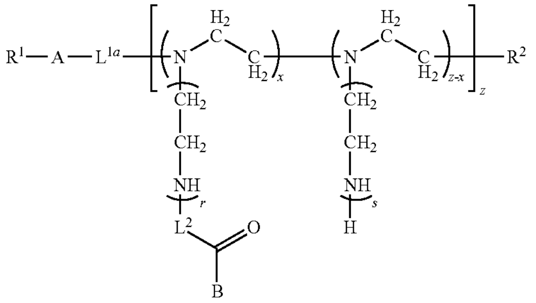

(IV)

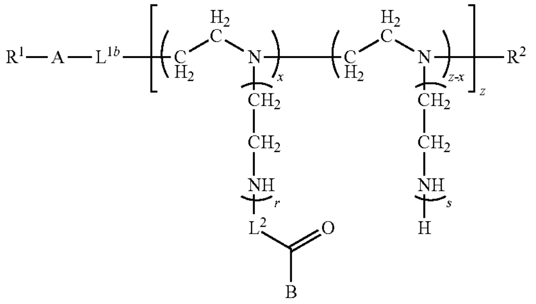

wherein $R^1$ and $R^2$ are each independently a hydrogen atom or an optionally substituted $C_{1-12}$ alkyl group, $R^3$ is a side chain of any amino acid, A is a single bond or a hydrophilic polymer chain, $L^{1a}$ and $L^{1b}$ are each independently a single bond or a linking group, $L^2$ is a single bond or $L^3$, $L^3$ is a linker represented by the formula (V) or (VI), (V)

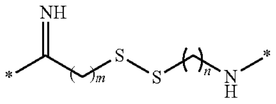

-continued (VI)

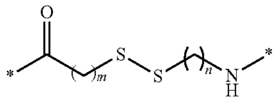

wherein m and n are each independently an integer of 0 to 5,

* on the left side is a bonding position to an —NH— group, and

* on the right side is a bonding position to a carbonyl group,

B is a $C_{1-20}$ haloalkyl group,

D is a cation-containing group, an anion-containing group, or a group represented by the formula (VII):

(VII)

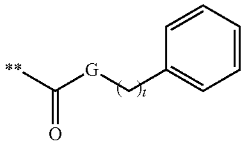

wherein t is an integer of 0 to 5,

** is a bonding position to a $-(CH_2)_q-$ group, and

G is O or NH,

E is an NHCOR group, an NHCOOR group, a CONHR group, or a COOR group,

R is an alkyl group having 3 to 20 carbon atoms or a group derived from a lipid, z is an integer of 2 to 500, x is an integer that is not less than 40% of z, y is an integer that may be 0, w is an integer that may be 0, z-x-y-w is an integer that may be 0, z-x is an integer that may be 0, p, q and r are each independently an integer of 1 to 10, and s is an integer of 0 to 10.

(provided that, in the formulas (III) and (IV), (i) when A is a single bond, (ii) m is an integer of 0 to 2).

In each of the above-mentioned formulas, the portion represented by the partial structure $[\ .\ .\ .\ ]_Z$ is a polymer containing a segment having a haloalkyl group as a side chain, which is the structural feature of the polymer of the present invention (hereinafter sometimes denoted as "haloalkylated segment"). The "haloalkylated segment" is each composed of one or more structural units and may be a polymer composed of one structural unit or a copolymer composed of two or more structural units. In the copolymer, the order of polymerization of each structural unit constituting the copolymer is not particularly limited and may be any, and the copolymer may be either a random copolymer or a block copolymer.

In the polymers of the present invention represented by the above-mentioned formulas (I) to (IV), such structural units are represented by the following partial structural formulas.

Polymer of the Formula (I) (Polypeptide Structures)

(I-a)

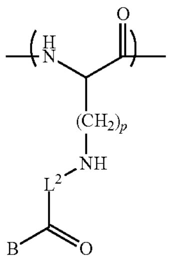

(I-b)

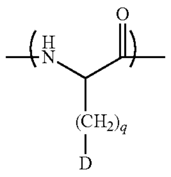

-continued (I-c)

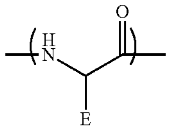

(I-d)

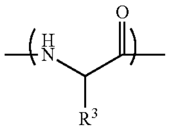

Polymer of the Formula (II) (Polypeptide Structures)

(II-a)

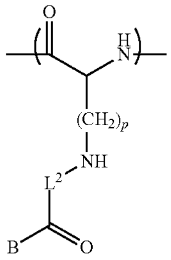

(II-b)

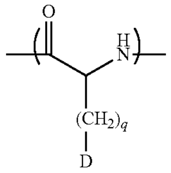

(II-c)

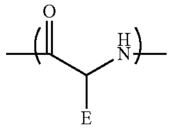

(II-d)

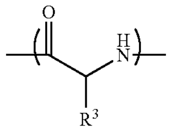

Polymer of the Formula (III) (Polyethyleneimine Structures)

(III-a)

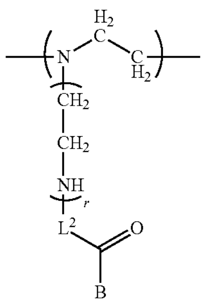

-continued (III-b)

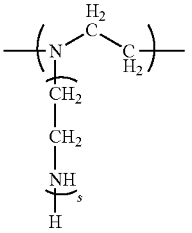

Polymer of the Formula (IV) (Polyethyleneimine Structures)

(IV-a)

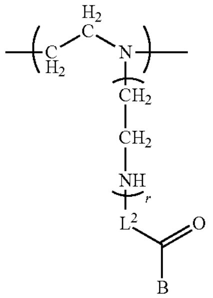

(IV-b)

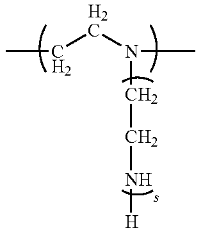

In the polymer of the present invention, structural units represented by the above-mentioned partial structural formulas (I-a), (II-a), (III-a), and (IV-a) are essential.

In the present specification, respective structural units represented by the above-mentioned partial structural formulas are sometimes denoted as "monomer" and "monomer (I-a)".

Each symbol in the formulas (I) to (IV) is defined in detail below.

(1) Polymer Portion Containing Haloalkylated Segment z indicates the total number of monomers constituting each polymer represented by the formulas (I) to (IV), and each z is independently an integer of 2 to 500.

x indicates the total number of monomer (Ia), monomer (II-a), monomer (III-a), and monomer (IV-a) that constitute the "haloalkylated segment" in respective polymers represented by the formulas (I) to (IV), and each x independently represents an integer of 40% or more of z.

In monomer (I-a) and monomer (II-a), each x is preferably independently an integer of not less than 50% of z.

y is the total number of monomer (I-b) and monomer (II-b) in each polymer represented by the formula (I) or (II), and each y independently represents an integer that may be 0. y may be, for example, an integer of not less than 1, an integer of not less than 2, or an integer of not less than 5. In addition, y may be, for example, an integer of not more than 200, an integer of not more than 100, an integer of not more than 80, an integer of not more than 40, or an integer of not more than 20.

w is the total number of monomer (I-c) and monomer (II-c) in each polymer represented by the formula (I) or (II), and each w independently represents an integer that may be 0. w may be, for example, an integer of not less than 1, an integer of not less than 2, or an integer of not less than 5. In addition, w may be, for example, an integer of not more than 200, an integer of not more than 100, an integer of not more than 80, an integer of not more than 40, or an integer of not more than 20.

As used herein, each "x+y+w" representing the total number of monomer (I-a) and monomer (I-b), monomer (II-a) and monomer (II-b), and monomer (I-c) and monomer (II-c), is preferably independently an integer of not less than 95% of z.

In addition, each "z-x-y-w" representing the total number of monomer (I-d) and monomer (II-d) in each polymer represented by the formula (I) or (II) is independently an integer that may be 0.

In monomer (III-a) and monomer (IV-a), each x is preferably independently an integer of not less than 50% of z.

In addition, each "z-x" representing the total number of monomer (III-b) and monomer (IV-b) in each polymer represented by the formula (III) or (IV) is independently an integer that may be 0.

B is a $C_{1-20}$ haloalkyl group.

The "$C_{1-20}$ haloalkyl group" is a linear or branched chain alkyl group having 1 to 20 carbon atoms in which one or more hydrogen atoms are substituted with a halogen atom. Examples of the "$C_{1-20}$ haloalkyl group" include bromomethyl, 2-bromoethyl, 3-bromopropyl, 4-bromobutyl, 5-bromopentyl, 6-bromohexyl, iodo methyl, 2-iodo ethyl, 3-iodo propyl, 4-iodo butyl, 5-iodo pentyl, 6-iodohexyl, fluoromethyl, 2-fluoroethyl, 3-fluoropropyl, 4-fluorobutyl, 5-fluoropentyl, 6-fluorohexyl, tribromomethyl, trichloromethyl, trifluoromethyl, difluoromethyl, perfluoroethyl, perfluoropropyl, perfluoroisopropyl, perfluorobutyl, perfluoroisobutyl, perfluoro-sec-butyl, perfluoro-tert-butyl, perfluoropentyl, perfluorohexyl, perfluoroisohexyl, perfluoro-1,1-dimethylbutyl, perbromo-2,2-dimethylbutyl, periodo-3,3-dimethylbutyl, perfluoro-2-ethylbutyl, perfluoroheptyl, perfluorooctyl, perfluoro-3-methyloctyl, perfluorononyl, perfluorodecyl, perfluoroundecyl, perfluorododecyl, perbromotridecyl, perfluorotetradecyl, periodopentadecyl, perfluorohexadecyl, perfluoroheptadecyl, perfluorooctadecyl, perfluorononadecyl, perfluoroicosyl, and the like.

The above-mentioned "$C_{1-20}$ haloalkyl group" may have one or more oxygen atoms, that form an ether bond, as a carbon chain-constituting atom at an insertable position. Specific preferable examples of such "$C_{1-20}$ haloalkyl group" (also denoted as "$C_{1-20}$ haloalkoxyalkyl group") include $CF_3OCF_2$—, $CF_3CF_2OCF_2$—, $(CF_3)_2CFOCF_2$—, $CF_3OCF_2CF_2$—, $CF_3CF_2OCF_2CF_2$—, $CF_3OCF_2CF_2OCF_2$—, $CF_3CF_2OCF_2CF_2OCF_2$—, $CF_3CF_2OCF_2CF_2OCF_2CF_2$—, $CF_3CF_2OCF_2CF_2OCF_2CH_2$—, $CF_3CF_2CF_2OCF(CF_3)$—, and $CF_3CF_2CF_2OCF(CF_3)$ $CF_2OCF(CF_3)$—.

As the "$C_{1-20}$ haloalkyl group", a $C_{1-20}$ alkyl group in which one or more hydrogen atoms are substituted with a fluorine atom is preferred, and a $C_{1-20}$ alkyl group in which all hydrogen atoms are substituted with a fluorine atom is more preferred.

As described above, D is a cation-containing group, an anion-containing group, or a group represented by the formula (VII).

(VII)

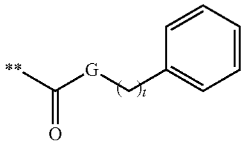

wherein t is an integer of 0 to 5,

** is a bonding position to a $-(CH_2)_q-$ group, and

G is O or NH.

Here, the "cation-containing group" represented by D is any suitable group containing a cation, such as a group containing an ammonium cation. Structural units having a cation-containing group (monomers (I-b) and (II-b)) are not essential in the polymer of the present invention. However, when the monomer is contained, a polycationic segment is formed within the haloalkylated segment, and the polymer of the present invention can more effectively form a complex with a biopolymer (e.g., siRNA) used as a drug, under physiological conditions. Specifically, a group selected from the group consisting of an amino group, an amidine group, and groups represented by the following (i) to (iv) derived from diethylenetriamine is a preferred "cation-containing group".

$$\text{-J-}(CH_2)_{l1}-(NH-(CH_2)_{m1}-)_{n1}-NH_2 \quad \text{(i)}$$

$$\text{-J-}(CH_2)_{l2}-N(-(CH_2)_{m2}-NH_2)_2 \quad \text{(ii)}$$

$$\text{-J-}(CH_2)_{l3}-N((-(CH_2)_{m3}-NH_2)(-(CH_2)_{m4}-NH-)_{n2}-H) \quad \text{(iii)}$$

$$\text{-J-}(CH_2)_{l4}-N(-(CH_2)_{m5}-N(-(CH_2)_{m6}-NH_2)_2)_2 \quad \text{(iv)}$$

wherein J is NH or CONH, l1-l4 and m1-m6 are preferably each independently an integer of 2 or 3, more preferably 2.

n1 and n2 are preferably each independently an integer of 1 to 3.

A more preferred "cation-containing group" is, for example, a group represented by the formula (i).

The structural units (monomers (I-b) and (II-b)) having the above-mentioned "cation-containing group" may have a thiol group (—SH group) at the end of the side chain, that is, at the end of the above-mentioned cation-containing group. Thiol groups react with each other to form a cross-linking reaction by a disulfide bond. As a result, the associating property between the polymers of the present invention is enhanced, and a polymer capable of forming highly stable micelles can be obtained. A disulfide bond is a bond that is easily cleaved under a reducing environment. Therefore, stable micelles can be maintained under a non-reducing environment outside the cell, and inclusions can be efficiently released under a reducing environment inside the cell.

Therefore, in one embodiment, D is $-NH^+=C(=NH)-(CH_2)_o-SH$ and o is an integer of 1 to 10, preferably an integer of 2-4.

Here, the "anion-containing group" represented by D is any suitable group containing an anion, such as a carboxyl group. Structural units having an anion-containing group (monomers (I-b) and (II-b)) are not essential in the polymer of the present invention. However, when the monomer is contained, a polyanion segment is formed within the haloalkylated segment, and the polymer of the present invention can more effectively form a complex with a biopolymer (e.g., platinum complex anticancer agents such as cisplatin, dachplatin, and the like) used as a drug, under physiological conditions. Specifically, carboxyl group is a preferred "anion-containing group".

Furthermore, monomers (I-b) and (II-b) having "a group represented by the formula (VII)" represented by D are not essential in the polymer of the present invention. However, when the monomer is contained, a polyanion segment is formed within the haloalkylated segment, and the polymer of the present invention can more effectively form a complex with a biopolymer (e.g., paclitaxel etc.) used as a drug, under physiological conditions.

The NHCOR group, NHCOOR group, CONHR group, or COOR group represented by E is a segment obtained by converting the end of the cation-containing $NH_2$ group represented by D or the anion-containing COOH group.

Specifically, the above-mentioned (i) is converted to the following (i'). The same applies to other groups.

$$\text{-J-}(CH_2)_{l1}-(NH-(CH_2)_{m1}-)_{n1}-NHCOR \quad \text{(i')}$$

wherein R is an alkyl group having 3 to 20 carbon atoms or a group derived from a lipid. As the "alkyl group having 3 to 20 carbon atoms", the aforementioned alkyl moiety for the "$C_{1-20}$ haloalkyl group" can be referred to. Examples of the "group derived from lipid" include a group obtained by removing a hydrogen atom from the OH group of tocopherol or cholesterol.

The monomer (I-c) and monomer (II-c) that constitute the "haloalkylated segment" in each polymer represented by formula (I) or (II) are each independently derived from any amino acid. Therefore, $R^3$ represents the "side chain of any amino acid" selected as monomers (Ic) and (II-c).

For example, monomer (I-c) and monomer (II-c) are each independently any appropriate cationic amino acid having a cationic group (e.g., amino group, guanidyl group, imidazoyl group, and the like) in the side chain. Examples include basic amino acids such as lysine, arginine, histidine, ornithine, and the like. Alternatively, a hydrophobic amino acid (e.g., leucine, isoleucine, valine, phenylalanine, proline, and the like) and a cationic amino acid may be included to increase the hydrophobicity of the cationic polyamino acid segment. Therefore, preferred examples of $R^3$ include side chains of such amino acids.

$L^2$ is a single bond or $L^3$, and $L^3$ is a linker represented by the formula (V) or (VI).

(V)

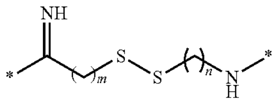

(VI)

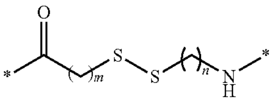

wherein m and n are each independently an integer of 0 to 5,

* on the left side is a bonding position to an —NH— group, and

* on the right side is a bonding position to a carbonyl group.

In each polymer represented by the formula (III) or (IV), (i) when A is a single bond, (ii) m is an integer of 0 to 2.

p, q, and r are each independently an integer of 1 to 10. s is an integer of 0 to 10.

(2) Hydrophilic Polymer Segment Portion A in each polymer represented by the formula (I) to (IV) is a single bond or a hydrophilic polymer chain. When A is a hydrophilic polymer chain, it corresponds to a "hydrophilic polymer segment".

The above-mentioned hydrophilic polymer chain can be composed of any appropriate hydrophilic polymer. Examples of the hydrophilic polymer include poly(ethylene glycol), polysaccharide, poly(vinylpyrrolidone), poly(vinylalcohol), poly(acrylamide), poly(acrylic acid), poly(methacrylamide), poly(methacrylic acid), poly(methacrylate), poly(acrylate), polyamino acid, poly(malic acid), poly(oxazoline), and derivatives thereof. Specific examples of the polysaccharide include starch, dextran, fructan, galactan, and the like. The polyethylene glycol may be polyethylene glycol end-modified with groups such as $C_1$-$C_6$ alkyl group and the like. Also, polyethylene glycols with various terminal functional groups for binding to cationic polyamino acid segments or linking groups (also referred to as "linker") are commercially available. In addition, polyethylene glycols of various molecular weights and branched types are commercially available, are readily available, and thus are preferably used.

The weight average molecular weight of the above-mentioned hydrophilic polymer segment may be preferably 10,000 to 80,000, more preferably 10,000 to 60,000, for example, 10,000 to 40,000, per one segment.

(3) Other Polymer Constituent Portions $L^{1a}$ and $L^{1b}$ in each polymer represented by the formula (I) to (IV) are each independently a single bond or a linking group.

When $L^{1a}$ and $L^{1b}$ are each a "linking group", it becomes a linking portion between the "haloalkylated segment" and the "hydrophilic polymer segment" in the polymer of the present invention.

Specifically, as the linking group represented by $L^{1a}$, a linking group selected from —NH—, —O—, —O-$L_4$-NH—, —CO—, —$CH_2$—, and a group represented by —O-$L_5$-S-$L_6$-NH— wherein $L_4$-$L_6$ are each independently a $C_{1-6}$ alkylene group can be mentioned. As the linking group represented by $L^{1b}$, a linking group selected from OCO-$L_7$-CO—, —NH— and —NHCO-$L_8$-CO— wherein $L_7$ and $L_B$ are each independently a $C_{1-6}$ alkylene group can be mentioned.

Examples of the "$C_{1-6}$ alkylene group" include —$CH_2$—, —$(CH_2)_2$—, —$(CH_2)_3$—, —$(CH_2)_4$—, —$(CH_2)_5$—, —$(CH_2)_6$—, —$CH(CH_3)$—, —$C(CH_3)_2$—, —$CH(C_2H_5)$—, —$CH(C_3H_7)$—, —$CH(CH(CH_3)_2)$—, —$(CH(CH_3))_2$—, —$CH_2$—$CH(CH_3)$—, —$CH(CH_3)$—$CH_2$—, —$CH_2$—$CH_2$—$C(CH_3)_2$—, —$C(CH_3)_2$—$CH_2$—$CH_2$—, —$CH_2$—$CH_2$—$CH_2$—$C(CH_3)_2$—, and —$C(CH_3)_2$—$CH_2$—$CH_2$—$CH_2$—.

In the above, a particularly preferred linking group includes —CO— for $L^{1a}$ and —NH— for $L^{1b}$.

The "$C_{1-12}$ alkyl group" of the optionally substituted $C_{1-12}$ alkyl group for $R^1$ or $R^2$ in each polymer represented by the formula (I) to (IV) is a "linear or branched chain alkyl group having 1 to 12 carbon atoms". As concrete examples thereof, methyl, ethyl, propyl, isopropyl, butyl, isobutyl, sec-butyl, tert-butyl, pentyl, isopentyl, neopentyl, 1-ethylpropyl, hexyl, isohexyl, 1,1-dimethylbutyl, 2,2-dimethylbutyl, 3,3-dimethylbutyl, 2-ethylbutyl, heptyl, octyl, 3-methyloctyl, nonyl, decyl, undecyl, dodecyl and the like can be mentioned.

The above-mentioned "$C_{1-12}$ alkyl group" is optionally substituted by 1 to 8 (preferably 1 to 5) substituents at substitutable positions. Examples of such substituent include azido group, alkynyl group (e.g., ethynyl, 1-propynyl, 2-propynyl, 1-butynyl, 2-butynyl, 3-butynyl, 1-pentynyl, 2-pentynyl, 3-pentynyl, 4-pentynyl, 1-hexynyl, 2-hexynyl, 3-hexynyl, 4-hexynyl, 5-hexynyl, 4-methyl-2-pentynyl etc.), thiol group, maleimide group, acetalformyl group, a cyano group, formyl group, carboxy group, amino group, $(C_{1-6})$ alkoxycarbonyl group, $(C_{2-7})$acylamido group, siloxy group, silyl amino group, and trialkyl siloxy group (alkylsiloxy groups are mutually independent and have 1 to 6 carbon atoms), and the like.

When the substituent in $R^1$ is, for example, a formyl group, a carboxy group, or an amino group, a target binding site may be bonded to the $C_{1-12}$ alkyl group via these substituents.

Here, the target binding site is a site having a biological recognition function that can specifically bind to a substance derived from a living organism or a virus to form a biological binding pair with the substance. Examples thereof include antibodies or fragments thereof, or proteins having other functionality or target directionality, peptides, aptamers, sugars such as lactose, physiologically active substances such as folic acid, sugars such as lactose and glucose, and the like.

The above-mentioned target binding site is, for example, preferably a peptide having a weight average molecular weight of 50 to 20,000, more preferably a peptide having a weight average molecular weight of 100 to 10,000, further preferably a peptide having a weight average molecular weight of 150 to 3,000.

In addition, the above-mentioned peptide is preferably a peptide having 1 to 200 amino acid residues, more preferably a peptide having 1 to 100 amino acid residues, further preferably a peptide having 1 to 30 amino acid residues.

Examples of the above-mentioned include peptides capable of specifically binding to integrins involved in angiogenesis, intimal hyperplasia, and proliferation of malignant tumors, and specific examples include RGD peptide. Here, the RGD peptide refers to a peptide containing an arginine-glycine-aspartic acid (RGD) sequence. Preferably, the RGD peptide may be a cyclic RGD (cRGD) peptide.

As described above, the polymer of the present invention can bind a target binding site as a substituent in $R^1$ in one embodiment thereof. The polymer of the present invention thus has a great advantage that it can function as a drug carrier having a target binding site. With this feature, the polymer of the present invention can effectively deliver drugs to the target sites.

In the polymer of the present invention, the structural units (monomers) constituting the above-mentioned "haloalkylated segment" may be the same or different. Taking monomer (I-a) as an example, the same monomer (I-a) (e.g., monomer wherein p is 1 (Ia-1(1)) may be polymerized, or two kinds of monomers (Ia) with different structures (e.g., monomer wherein p is 1 (Ia-1(1)) and monomer wherein p is 10 (Ia-1(2)) may be polymerized. Those of ordinary skill in the art can perform the present invention by selecting as appropriate according to the purposes.

Although not limited, a preferred polymer of the present invention is, for example, a polymer represented by the formula (I) or (II), and particularly, a polymer in which A is a hydrophilic polymer chain, and z-x-y or z-x-y-w is 0.

II. Production of the Polymer of the Present Invention

The polymer of the present invention can be appropriately produced by a method known per se that is generally used in the pertinent technique field by those skilled in the art. In the production of the polymer of the present invention, the starting material monomers and the like can be produced by a method known per se. When it is marketed, the commercially available product can be used.

Specifically, the polymer can be produced by combining as appropriate:

i) a step of sequentially polymerizing a hydrophilic polymer chain prepared in advance and a predetermined monomer (I-a)-(I-c), (II-a)-(II-c), (III-a), (III-b), (IV-a), or (IV-b) according to the target polymer structure, or ii) a step of binding prepolymerized haloalkylated segments with hydrophilic polymer segments; and introducing other groups (e.g., haloalkyl group) constituting the polymer of the present invention.

More specifically, for example, N-carboxylic acid anhydride (NCA) of a given amino acid (monomer) to which a protecting group has been introduced as necessary is polymerized sequentially using, as an initiator, the terminal amino group of a hydrophilic polymer (e.g., polyethylene glycol) aminated at the ω terminal, and then the haloalkyl group may then be introduced and converted to a haloalkylated segment by deprotection or side chain conversion. A block copolymer having a haloalkylated segment may be synthesized by first synthesizing a polyamino acid having a protective group introduced as necessary, then binding same with a hydrophilic polymer, followed by deprotection or side chain conversion as necessary. Various methods are used for binding polyamino acid and hydrophilic polymer, and a typical method includes introducing a reactive functional group into each end and then allow coupling thereof. Examples thereof include a method of binding a carboxy group and an amino group by using a condensing agent or by active esterification, a method using maleimide and thiol, and a method using so-called click chemistry using alkyne and azide.

Structural design and synthesis planning of the polymer of the present invention can be performed as appropriate by those of ordinary skill in the art. For example, when a drug that forms a complex is a "nucleic acid", the ratio between the number of amines (N) contained in the polymer and the number of phosphate groups (P) contained in the nucleic acid can be controlled by adjusting the mixing ratio of the polymer and the nucleic acid. Although not limited, for example, the N/P ratio can be designed to fall within the range of 0.1 to 5.0.

III. Use of the Polymer of the Present Invention as Drug Carrier (1) Polymer-Drug Complex The polymer of the present invention can form a complex (e.g., polyion complex (PIC)) by interaction with a drug. The polymer of the present invention improves the stability of the "polymer-drug complex" through effects attributed to the "haloalkylated segment" (e.g., effect of interaction between polyfluorinated compounds). This makes it possible to improve the retention property in blood and improve the clinical efficacy of the drug.

The polymer of the present invention can also form a polymer-drug complex by covalently binding with a drug.

(2) Target Drug

The drug to which the polymer of the present invention is applied is not particularly limited. Preferable examples thereof include anionic compounds having more negative charges than positive charges in an aqueous medium at physiological pH (e.g., pH 7.4). From this aspect, biopolymers are preferred.

Here, the biopolymer refers to a polymer derived from living organisms and a polymer structurally similar thereto. Specifically, protein, lipid, and nucleic acid can be mentioned. The above-mentioned biopolymer is preferably at least one selected from the group consisting of proteins and nucleic acids. Here, the protein includes peptides.

The above-mentioned nucleic acid means a poly or oligonucleotide whose basic unit is a nucleotide consisting of a purine or pyrimidine base, a pentose, and phosphoric acid, and oligo- or poly-double-stranded RNA, oligo- or poly-double-stranded DNA, oligo- or poly-single-stranded DNA, and oligo- or poly-single-stranded RNA can be mentioned. It also includes oligo- or poly-double-stranded nucleic acid and oligo- or poly-single-stranded nucleic acid in which RNA and DNA are mixed on the same strand. Nucleotide contained in nucleic acid may be of a natural or chemically-modified non-natural type, and may be those to which molecules such as amino group, thiol group, fluorescent compound, and the like have been added. Although not limited, the nucleic acid may consist of 4 to 20,000 bases, preferably 10 to 10,000 bases, further preferably 12 to 30 bases. In consideration of the function or action, moreover, plasmid DNA, siRNA, microRNA, mRNA, shRNA, antisense nucleic acid, decoy nucleic acid, aptamer and ribozyme can be mentioned.

Another preferred example of drugs to which the polymer of the present invention is applied is platinum complex anticancer agents such as cisplatin and dachplatin, which can form a complex via coordinate bonds.

Another preferred example of drugs to which the polymer of the present invention is applied is hydrophobic anticancer agents such as paclitaxel, which can form a complex via hydrophobic interactions.

The drug to which the present invention is applied may not have or may have a haloalkyl group added thereto. Such chemical modification can be appropriately performed by those of ordinary skill in the art in view of the structure of the target drug.

(3) Preparation of Polymer-Drug Complex

A polymer-drug complex can be prepared by those of ordinary skill in the art according to a method known per se. For example, it can be prepared by stirring a mixture of the polymer of the present invention and a drug while applying energy from ultrasonic irradiation. In addition, the above-mentioned complex can be prepared by, for example, mixing the polymer of the present invention and a drug in any bufferized aqueous solution (e.g., Tris buffer, phosphate buffered saline, HEPES buffer, etc.).

The size of the above-mentioned complex can be set to any appropriate size according to the purpose. For example, an average particle size by dynamic light scattering (DLS) is preferably 5 nm to 200 nm, more preferably 10 nm to 100 nm.

(4) Medicament Composed of Polymer-Drug Complex

The polymer-drug complex of the present invention can be administered as it is or in the form of a pharmaceutical composition containing the complex as an active ingredient, as a drug (drug delivery preparation) to a subject in need of the administration.

The subject of administration preferably includes mammals such as human, dog, cat, horse, cow, and other mammals. Humans are particularly preferred as the subject of administration.

In formulating a preparation, a drug, which is an active ingredient, may be mixed with a carrier or diluent and additives to form a pharmaceutical composition. Where necessary, other drugs to be used in combination may be contained in the pharmaceutical composition.

As the dosage form, parenteral preparations such as injection, drip transfusion and the like are preferred.

Examples of the carrier or diluent include aqueous solvents, for example, distilled water, sterile water, Ringer solution, saline, buffer, and the like.

Examples of the additive include pharmaceutically acceptable fillers, dispersing agents, buffering agents, preservatives, solubilizing agents, stabilizers, isotonicity agents, pH adjusters, and the like.

Examples of the preferred administration route include intravenous administration, intraarterial administration, intracerebral administration, and the like.

The content of the drug in a pharmaceutical composition and administration method (dosage, dose) can be appropriately determined by those of ordinary skill in the art according to individual circumstances such as specific embodiment of the polymer of the present invention, drugs to be used, and the like.

Taking the case of using a nucleic acid as a drug as an example, for humans, the dose of the above-mentioned nucleic acid is, without limitation, about 0.0001 mg to about 1,000 mg, per dose per 1 kg body weight of an adult, based on siRNA molecules or antisense nucleic acid molecules. The dose or dosage is generally selected in consideration of the gender, age, and body weight of the subject of administration, symptoms, severity, side effects, and the like. The administration can be performed at intervals of, for example, 1 week, 2 weeks, 3 weeks, or 4 weeks, or more than one month if necessary. As the administration route, as described above, for example, intravenous administration, intraarterial administration, intracerebral administration, and the like are selected.

EXAMPLES

Hereinafter, the present invention is described in more detail in the following with reference to Production Examples of the polymer of the present invention, Formulation Examples of complexes with the drug, and animal Experimental Examples for evaluating the efficacy thereof. However, these do not limit the present invention, and may be changed without departing from the scope of the present invention.

1. Reagent•Cell•Experiment Animal, Etc.

(1) Synthesis Reagent

PEG-$NH_2$ was purchased from NOF CORPORATION (product name: SUNBRIGHT MEPA-12T). Methanol, thiourea, N,N-dimethylformamide (DMF), calcium hydride, and triethylamine were purchased from FUJIFILM Wako Pure Chemical Corporation. DMF was used after purification by distillation under reduced pressure in the coexistence of calcium hydride before use. N-carboxylic acid anhydride of ε-trifluoroacetyl-L-lysine was purchased from Chuo Kaseihin Co., Inc. Diethyl ether was purchased from Showa Ether Co., Ltd. Dialysis tube was purchased from SPECTRUM. $C_7F_{15}$—$COOCH_3$ (hereinafter also denoted as "Rf-A"; refer to the following structural formula on the left) and $C_5F_{11}O_2COOCH_3$ (hereinafter also denoted as "Rf-B"; refer to the following structural formula on the right) used were commercially available products.

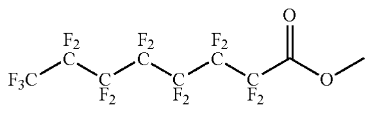

-continued

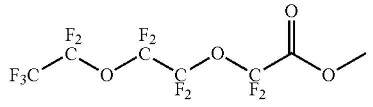

In the following, the "haloalkyl group" introduced into a polymer and the like by a reaction with the above-mentioned Rf-A or Rf-B is sometimes to be abbreviated as Rf group, one derived from Rf-A is sometimes abbreviated as Rf-1 group, and one derived from Rf-B is sometimes abbreviated as Rf-2 group.

(2) Nucleic Acid

A single-stranded antisense oligo nucleic acid (ASO) and heteronucleic acid (HDO) consisting of a double strand of ASO and a complementary strand were used (purchased from GeneDesign). Both ASO and HDO targeted mouse MALAT1 (metastasis associated in lung adenocarcinoma transcript-1) sequence.

2. Synthesis of Polyethylene Glycol-Poly(L-Lysine) Block Copolymer into which Rf Group has been Introduced (PEG-PLys(Rf)) (Production of the Polymer of the Present Invention)

(1) 300 mg of PEG-$NH_2$ having an average molecular weight of 12,000 and 456 mg of thiourea were dissolved in 6 mL of N,N-dimethylformamide (DMF). Next, the obtained solution was added to a solution of 310 mg of ε-trifluoroacetyl-L-lysine N-carboxylic acid anhydride (Lys(TFA)-NCA) and 456 mg of thiourea dissolved in 6 mL of DMF, and the mixture was reacted at 25° C. for 3 days. The reaction solution was added dropwise to 200 mL of a mixed solvent of diethyl ether/methanol (v/v: 15/1) to obtain a white precipitate. Further, the precipitate was dissolved in methanol and added dropwise into 200 mL of diethyl ether, which was repeated twice. The obtained white precipitate was filtered and dried in vacuum to obtain PEG-PLys (TFA).

200 mg of the obtained PEG-PLys (TFA) was dissolved in 18 mL of methanol, 2 mL of 1M sodium hydroxide solution was added, and the mixture was reacted at 35° C. for 24 hr. The reaction solution was placed in a dialysis tube (molecular weight cut off 6,000-8,000 Da) and dialyzed four times with 0.01M NaOH solution as the external liquid and three times with pure water as the external liquid. The dialysis membrane internal solution was collected and freeze-dried to obtain PEG-PLys as a white powder. It was confirmed by $^1$H-NMR that the obtained compound was the desired product, and the PLys degree of polymerization was 40. The structure is described below.

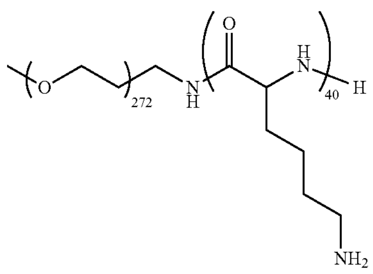

(2) 20 mg of PEG-PLys was dissolved in 2 mL of methanol and 1.2 equivalents of triethylamine relative to the primary amino group of PEG-PLys, 0.1, 0.3, and 0.5 equivalents of Rf-A or Rf-B relative to the primary amino group of PEG-PLys was added and the mixture was reacted overnight with stirring.

Each reaction solution was placed in a dialysis tube and dialyzed twice with methanol (not less than 12 hr each time), 3 times with 10 mM phosphate buffer (pH 7.4) (not less than 2 hr each time), 3 times with 100 mM NaCl aqueous solution (not less than 2 hr each time), and 3 times with pure water (not less than 2 hr each time). The reaction solution was freeze-dried to obtain PEG-PLys (Rf-AX) and PEG-PLys (Rf-BX) (X corresponds to the charged amount of 0.1, 0.3, and 0.5) as a white powder.

3. Preparation of Polymer-Drug Complex Particles by Mixing Nucleic Acid and PEG-PLys(Rf)

ASO, HDO and Rf-1-HDO (hereinafter sometimes simply referred to as "Rf-HDO") were prepared using 10 mM HEPES (pH 7.3) so as to respectively have concentrations of 80 μM, 40 μM. PEG-PLys (control polymer), PEG-PLys (Rf-A0.3) (the polymer of the present invention) and PEG-PLys(Rf-B0.5) (the polymer of the present invention) were prepared using 10 mM HEPES (pH 7.3) to have a concentration of 1 mg/mL. Each solution was mixed at the following mixing ratio (volume ratio) and stirred for 1 min with a vortex to prepare particles.

(preparing particle 1)

complex with PEG-PLys (N/P ratio=1.4)

nucleic acid/PEG-PLys/HEPES=60/47/133

(preparing particle 2)

complex with PEG-PLys (Rf-A0.3) (N/P ratio=1.2)

nucleic acid/PEG-PLys (Rf-A0.3)/HEPES=60/71/109

(preparing particle 3)

complex with PEG-PLys (Rf-B0.5) (N/P ratio=1.4) ((N/P ratio=1.4)

nucleic acid/PEG-PLys (Rf-B0.5)/HEPES=60/123/57

*) N/P ratio: ratio when the number of primary amines in the polymer is [N] and the number of phosphate groups in the nucleic acid is [P] (=ratio of positive electric charge and negative electric charge)

4. Animal Experiment (Retention Property in Blood)

(1) Particles Subjected to Test

Using AlexaFluoro647-labeled ASO and HDO (labeled by conventional method), a nucleic acid, and complex particles prepared under conditions described in the above-mentioned 3 were evaluated in animal experiments.

1) particles using ASO as nucleic acid (ASO series) test particle A: single labeled ASO (used as control 1) (20 μM solution (200 μL) was administered) (denoted as "Naked ASO" in FIG. 1)

test particle B: polymer-ASO complex (used as control 2) prepared under conditions of the above-mentioned 3. (preparing particle 1) (denoted as "ASOxLys" in FIG. 1)

test particle 1: polymer-ASO complex prepared under conditions of the above-mentioned 3. (preparing particle 2) (denoted as "ASOxRf-1" in FIG. 1)

test particle 2: polymer-ASO complex prepared under conditions of the above-mentioned 3. (preparing particle 3) (denoted as "ASOxRf-2" in FIG. 1)

2) particles using HDO as nucleic acid (HDO series)

test particle C: single labeled HDO (used as control 1) (10 μM solution (200 μL) was administered) (denoted as "Naked HDO" in FIG. 2)

test particle D: polymer-HDO complex (used as control 2) prepared under conditions of the above-mentioned 3. (preparing particle 1) (denoted as "HDOxLys" in FIG. 2)

test particle 3: polymer-HDO complex prepared under conditions of the above-mentioned 3. (preparing particle 2) (denoted as "HDOxRf-1" in FIG. 2)

test particle 4: polymer-HDO complex prepared under conditions of the above-mentioned 3. (preparing particle 3) (denoted as "HDOxRf-2" in FIG. 2)

3) particles using HDO modified with Rf-1 group as nucleic acid (Rf-HDO series)

test particle E: single labeled Rf-1-HDO (used as control 1) (denoted as "Naked Rf-HDO" in FIG. 3)

test particle F: polymer-Rf-1-HDO complex (used as control 2) prepared under conditions of the above-mentioned 3. (preparing particle 1) (denoted as "Rf-HDOxLys" in FIG. 3)

test particle 5: polymer-Rf-1-HDO complex prepared under conditions of the above-mentioned 3. (preparing particle 2) (denoted as "Rf-HDOxRf-1" in FIG. 3)

test particle 6: polymer-Rf-1-HDO complex prepared under conditions of the above-mentioned 3. (preparing particle 3) (denoted as "Rf-HDOxRf-2" in FIG. 3)

(2) Evaluation of Retention Property in Blood

200 μL of each of the above-mentioned test particles was administered from the tail vein of mice. Blood samples were collected from the tail vein 10 min, 30 min, 60 min, 180 min after administration. Fluorescence intensity in blood was measured with a fluorescence microplate reader (Tecan, Spark) and the residual amount in blood (Dose %/g) was quantified.

(3) Evaluation Results

The evaluation results are shown in FIG. 1-FIG. 3 described below.

FIG. 1 shows the evaluation results when ASO was used as the nucleic acid.

FIG. 2 shows the evaluation results when HDO was used as the nucleic acid.

FIG. 3 shows the evaluation results when HDO modified with Rf-1 group was used as the nucleic acid.

In each Figure, the horizontal axis shows the time after administration, and the vertical axis shows blood concentration (Dose %/g).

From the above evaluation results, it was clarified that the retention property of nucleic acids in blood is greatly improved by forming a complex with the haloalkylated polymer of the present invention (FIGS. 1 and 2). Furthermore, it was also clarified that the same improvement effect can be obtained even when a haloalkylated nucleic acid is used to form a complex with the haloalkylated polymer of the present invention (FIG. 3).

INDUSTRIAL APPLICABILITY

The present invention provides a polymer useful as a carrier in effectively delivering a drug such as nucleic acid medicine or the like to a target site, and is useful, for example, in the field of pharmaceutical product industry.

Where a numerical limit or range is stated herein, the endpoints are included. Also, all values and subranges within a numerical limit or range are specifically included as if explicitly written out.

As used herein the words "a" and "an" and the like carry the meaning of "one or more."

Obviously, numerous modifications and variations of the present invention are possible in light of the above teachings. It is therefore to be understood that, within the scope of the appended claims, the invention may be practiced otherwise than as specifically described herein.

All patents and other references mentioned above are incorporated in full herein by this reference, the same as if set forth at length.

The invention claimed is:

1. A polymer represented by the following formula (I), (II), (III), or (IV):

(I)

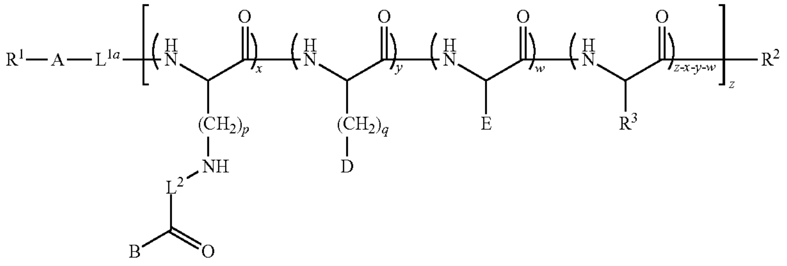

(II)

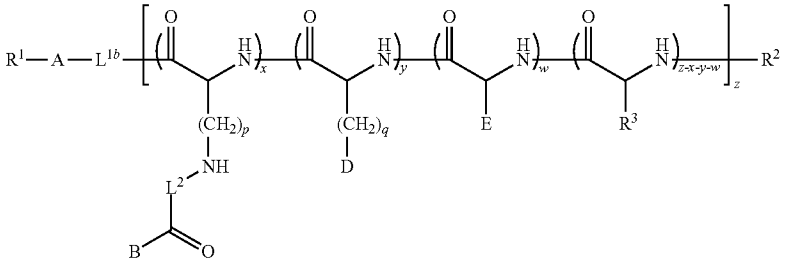

(III)

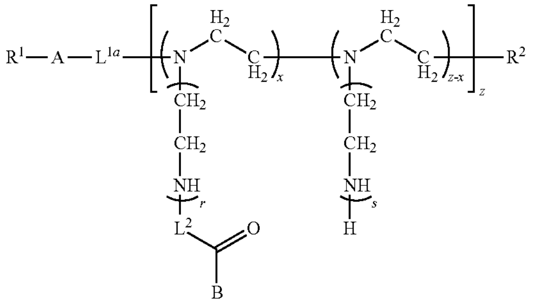

(IV)

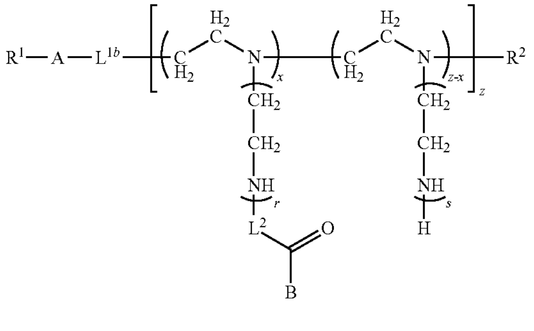

wherein $R^1$ and $R^2$ are each independently a hydrogen atom or an optionally substituted $C_{1-12}$ alkyl group, $R^3$ is a side chain of any amino acid, A is a single bond or a hydrophilic polymer chain, $L^{1a}$ and $L^{1b}$ are each independently a single bond or a linking group, $L^2$ is a single bond or $L^3$, $L^3$ is a linker represented by the formula (V) or (VI):

(V)

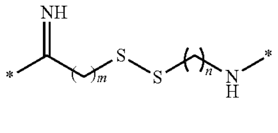

-continued (VI)

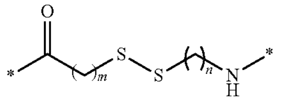

wherein m and n are each independently an integer of 0 to 5,

* on the left side is a bonding position to an —NH— group, and

* on the right side is a bonding position to a carbonyl group,

B is a $C_{2-20}$ perfluoroalkyl ether group having one or more ether bonds in the carbon chain, D is a cation-containing group, an anion-containing group, or a group represented by the formula (VII):

(VII)

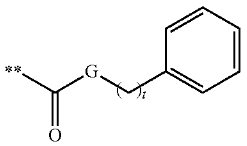

wherein t is an integer of 0 to 5,

** is a bonding position to a —$(CH_2)$q— group, and

G is O or NH,

E is an NHCOR group, an NHCOOR group, a CONHR group, or a COOR group,

R is an alkyl group having 3 to 20 carbon atoms or a group derived from a lipid, z is an integer of 2 to 500, x is an integer that is not less than 40% of z, y is an integer that may be 0, w is an integer that may be 0, z-x-y-w is an integer that may be 0, z-x is an integer that may be 0, p, q and r are each independently an integer of 1 to 10, and s is an integer of 0 to 10.

provided that, in the formulas (III) and (IV), (i) when A is a single bond, then (ii) m is an integer of 0 to 2.

2. The polymer according to claim 1, wherein, in the formula (I) or (II), a total of x, y, and w is not less than 95% of z.

3. The polymer according to claim 1, wherein A is a hydrophilic polymer chain.

4. The polymer according to claim 1, wherein A is a single bond.

5. A polymer-drug complex comprising a polymer according to claim 1 and a drug, wherein the polymer and the drug form a complex.

6. The polymer-drug complex according to claim 5, wherein the drug is a biopolymer.

7. A medicament comprising the polymer-drug complex according to claim 5 as an active ingredient.

* * * * *